US012636423B2

(12) United States Patent
Sivadas

(10) Patent No.: US 12,636,423 B2
(45) Date of Patent: May 26, 2026

(54) MAGNETIC CONTROL OF FLUID IN A FLUID MANAGEMENT SYSTEM

(71) Applicant: Alcon Inc., Fribourg (CH)

(72) Inventor: Kulangara Sivadas, Foothill Ranch, CA (US)

(73) Assignee: Alcon Inc., Fribourg (CH)

( * ) Notice: Subject to any disclaimer, the term of this patent is extended or adjusted under 35 U.S.C. 154(b) by 744 days.

(21) Appl. No.: 18/066,328

(22) Filed: Dec. 15, 2022

(65) Prior Publication Data

US 2023/0233747 A1 Jul. 27, 2023

Related U.S. Application Data

(60) Provisional application No. 63/267,158, filed on Jan. 26, 2022.

(51) Int. Cl.
*A61F 9/007* (2006.01)
*A61M 1/00* (2006.01)

(52) U.S. Cl.
CPC ........... *A61M 1/81* (2021.05); *A61F 9/00736* (2013.01); *A61B 2217/005* (2013.01); *A61B 2217/007* (2013.01); *A61M 2205/0272* (2013.01)

(58) Field of Classification Search
CPC ......... A61B 2217/005; A61B 2218/001; A61F 9/00736; A61F 9/007; A61M 1/774; A61M 2205/0272; A61M 2210/0612; A61M 3/0258
See application file for complete search history.

(56) References Cited

U.S. PATENT DOCUMENTS

| | | |
|---|---|---|
| 9,702,355 B2 | 7/2017 | Bourne |
| 10,470,926 B2 | 11/2019 | Zacharias |
| 10,537,471 B2 | 1/2020 | Bourne |
| 10,690,127 B2 | 6/2020 | Ochoa |
| 2007/0274840 A1 | 11/2007 | Ehben et al. |
| 2011/0313343 A1 | 12/2011 | Milutinovic et al. |

(Continued)

FOREIGN PATENT DOCUMENTS

WO 1993017729 A1 9/1993

OTHER PUBLICATIONS

Al-Habahbeh, et al., "Review of magnetohydrodynamic pump applications," Alexandria Engineering Jounal, vol. 55, Issue 2, Jun. 2016, pp. 1347-1358 (12 pages).

(Continued)

*Primary Examiner* — Deanna K Hall

(57) ABSTRACT

A fluid management system for an ophthalmic surgical system includes an irrigation system and an aspiration system. The irrigation system carries fluid toward a hand-piece and includes an irrigation pump or a plurality of pumps. The aspiration system carries fluid away from the handpiece and includes an aspiration pump or the plurality of pumps. The pumps include at least one magnetic pump configured to move the fluid. The magnetic pump includes a plug system and a magnetic field system. The plug system includes one or more plugs disposed within a housing, where each plug comprises a magnetic material. The magnetic field system generates a magnetic field to move one or more of the plugs in order to move the fluid in a pumping direction.

15 Claims, 11 Drawing Sheets

(56) References Cited

U.S. PATENT DOCUMENTS

| | | | | |
|---|---|---|---|---|
| 2015/0202082 | A1* | 7/2015 | Ilios | A61F 9/00781 |
| | | | | 604/9 |
| 2020/0353133 | A1 | 11/2020 | Gao et al. | |
| 2021/0100937 | A1 | 4/2021 | Bourne et al. | |
| 2022/0409431 | A1* | 12/2022 | Algawi | F16K 31/082 |

OTHER PUBLICATIONS

Commissariat, Tushna, "Ferrofluid pump has no moving parts," Physics World, Sep. 26, 2011 (5 pages).

Wikipedia, "Coilgun", Retrieved from https://en.wikipedia.org/w/index.php?title=Coilgun&oldid=1002028671; page last edited on Jan. 22, 2021 (9 pages).

Wikipedia, "Electromagnetic pump", Retrieved from https://en.wikipedia.org/w/index.php?title=Electromagnetic_pump&oldid=831186419; page last edited Mar. 19, 2018 (2 pages).

Leport, et al., "A magnetically driven piston pump for ultra-clean applications," © 2011 American Institute of Physics, Rev. Sci. Instrum. 82, 105114 (2011) (5 pages).

Mamiya, et al., "Practical Solution for Effective Whole-Body Magnetic Fluid Hyperthermia Treatment," Journal of Nanomaterials, vol. 2017; Published Dec. 13, 2017 (8 pages).

Mefford, et al., "Field-induced motion of ferrofluids through immiscible viscous media: Testbed for restorative treatment of retinal detachment," Journal of Magnetism and Magnetic Materials, vol. 311, Issue 1, Apr. 2007, (Available Dec. 18, 2006); pp. 347-353 (7 pages).

Pamme, Nicole, "Magnetism and microfluidics," Lab Chip. Jan. 2006 ;6(1):24-38 (First Published Nov. 28, 2005) (15 pages).

Paschalis, et al., "A Novel Implantable Glaucoma Valve Using Ferrofluid," PLOS ONE, www.plosone.org, Jun. 2013 | vol. 8 | Issue 6 (13 pages).

Qian, et al., "Magneto-Hydrodynamics Based Microfluidics," Mechanics Research Communications 36 (2009) pp. 10-21 (available online Jul. 4, 2008) (12 pages).

Raj, et al., "Advances in ferrofluid technology," Journal of Magnetism and Magnetic Materials, 149 (Aug. 1995) pp. 174-180 (8 pages).

Song, et al., "Electromagnetic Regulation of Electrolyte Solution Heat Convection in Microchannels," Micromachines 2018, 9, 262 (www.mdpi.com/journal/micromachines); Published May 28, 2018 (13 pages).

* cited by examiner

SYSTEM
10

CONSOLE
100

DISPLAY
SCREEN
104

FLUIDICS
SUBSYSTEM
110

HANDPIECE
112

102
HOUSING

108
INTERFACE
DEVICE

MAGNETIC CONTROL OF FLUID IN A FLUID MANAGEMENT SYSTEM

PRIORITY CLAIM

This application claims the benefit of priority of U.S. Provisional Patent Application Ser. No. 63/267,158 titled "Magnetic Control of Fluid in a Fluid Management System", filed on Jan. 26, 2022, whose inventor is Kulangara Sivadas, which is hereby incorporated by reference in its entirety as though fully and completely set forth herein.

TECHNICAL FIELD

The present disclosure relates generally to fluid management systems, and more particularly to magnetic control of fluid in a fluid management system.

BACKGROUND

Certain ophthalmic procedures involve moving fluid into and out from the eye. For example, in cataract surgery, the cataractous lens is removed by fragmenting the lens and aspirating the lens fragments from the eye. As another example, in a vitrectomy procedure, the vitreous is removed and replaced with a surgical fluid. During these procedures, a fluidics system moves fluid into and out from the eye to maintain a target intraocular pressure (IOP) of the eye. The fluidics system includes pumps that move the fluid. Known pumps, however, have deficiencies such that they do not effectively or efficiently move fluid.

BRIEF SUMMARY

In certain embodiments, a fluid management system for an ophthalmic surgical system includes an irrigation system and an aspiration system. The irrigation system is in fluid communication with a handpiece and carries fluid toward the handpiece. The irrigation system includes an irrigation pump of a plurality of pumps. The irrigation pump moves the fluid toward the handpiece. The aspiration system is in fluid communication with the handpiece and carries fluid away from the handpiece. The aspiration system includes an aspiration pump of the plurality of pumps. The aspiration pump moves the fluid away from the handpiece. The pumps include at least one magnetic pump configured to move the fluid. The magnetic pump includes a plug system and a magnetic field system. The plug system includes one or more plugs disposed within a housing, where each plug comprises a magnetic material. The magnetic field system generates a magnetic field to move one or more of the plugs in order to move the fluid in a pumping direction.

Embodiments may include none, one, some, or all of the following features: The magnetic field system includes a coil system that generates the magnetic field. The coil system includes one or more electromagnetic coils disposed about the housing. The coil system may comprise coils comprising first and second coils. The first coil generates the magnetic field to move the plug. The second coil is successive to the first coil and generates the magnetic field to continue to move the plug in the pumping direction. Windings may form the coils. The magnetic field system includes a magnet system that generates the magnetic field. The magnet system includes one or more magnets disposed about the housing. A magnet may move to yield a moving magnetic field that moves the plug in the pumping direction. The housing comprising tubing or a chamber with a rectangular box shape. The magnetic field system may generate the magnetic field in a direction substantially parallel to the pumping direction or in a direction substantially orthogonal to the pumping direction. The irrigation pump and/or the aspiration pump may be a magnetic pump. The fluid management system includes a controller that coordinates operation of magnetic pumps.

In certain embodiments, a handpiece for an ophthalmic surgical system includes an irrigation channel, an aspiration channel, and a magnetic pump. The irrigation channel is in fluid communication with an irrigation system and carries fluid from the irrigation system. The aspiration channel is in fluid communication with an aspiration system and carries fluid toward the aspiration system. The magnetic pump moves the fluid and includes a plug system and a magnetic field system. The plug system includes one or more plugs disposed within a housing, where each plug comprises a magnetic material. The magnetic field system generates a magnetic field to move one or more of the plugs in order to move the fluid in a pumping direction.

Embodiments may include none, one, some, or all of the following features: The pumping direction moving the fluid from the irrigation system or moving the fluid toward the aspiration system In certain embodiments, a fluid management system for an ophthalmic surgical system includes an irrigation system and an aspiration system. The irrigation system is in fluid communication with a handpiece and carries fluid in a housing toward the handpiece. The fluid comprises ferromagnetic nanoparticles to yield a ferrofluid. The irrigation system includes an irrigation pump of a plurality of pumps. The irrigation pump moves the fluid toward the handpiece. The aspiration system is in fluid communication with the handpiece and carries fluid in the housing away from the handpiece. The aspiration system includes an aspiration pump of the plurality of pumps. The aspiration pump moves the fluid away from the handpiece. The pumps include at least one magnetic pump configured to move the fluid. The magnetic pump includes a magnetic field system that generates a magnetic field to move the fluid with the ferromagnetic nanoparticles in a pumping direction.

Embodiments may include none, one, some, or all of the following features: The magnetic field system includes a coil system that generates the magnetic field. The coil system includes one or more electromagnetic coils disposed about the housing. The coil system may comprise coils comprising first and second coils. The first coil generates the magnetic field to move the plug. The second coil is successive to the first coil and generates the magnetic field to continue to move the plug in the pumping direction. Windings may form the coils. The magnetic field system includes a magnet system that generates the magnetic field. The magnet system includes one or more magnets disposed about the housing. A magnet may move to yield a moving magnetic field that moves the plug in the pumping direction. The housing comprising tubing or a chamber with a rectangular box shape. The magnetic field system may generate the magnetic field in a direction substantially parallel to the pumping direction or in a direction substantially orthogonal to the pumping direction. The irrigation pump and/or the aspiration pump may be a magnetic pump. The fluid management system includes a controller that coordinates operation of magnetic pumps.

In certain embodiments, a handpiece for an ophthalmic surgical system includes an irrigation channel, an aspiration channel, and a magnetic pump. The irrigation channel is in fluid communication with an irrigation system and carries fluid from the irrigation system. The fluid includes ferromagnetic nanoparticles to yield a ferrofluid. The aspiration channel is in fluid communication with an aspiration system and carries fluid toward the aspiration system. The magnetic pump moves the fluid and includes a magnetic field system. The magnetic field system generates a magnetic field to move one or more of the plugs in order to move the fluid comprising the ferromagnetic nanoparticles in a pumping direction.

Embodiments may include none, one, some, or all of the following features: The pumping direction moving the fluid from the irrigation system or moving the fluid toward the aspiration system.

In certain embodiments, a fluid management system for an ophthalmic surgical system includes an irrigation system and an aspiration system. The irrigation system is in fluid communication with a handpiece and carries fluid toward the handpiece. The fluid comprises an electrolyte. The irrigation system includes an irrigation pump of a plurality of pumps. The irrigation pump moves the fluid toward the handpiece. The aspiration system is in fluid communication with the handpiece and carries fluid away from the handpiece. The aspiration system includes an aspiration pump of the plurality of pumps. The aspiration pump moves the fluid away from the handpiece. The plurality of pumps include at least one magnetic pump configured to move the fluid. The magnetic pump includes a housing, an electrode pair, and a magnetic field system. The housing carries the fluid. The electrode pair generates an electric field through the housing. The magnetic field system generates a magnetic field to move the fluid through the housing in a pumping direction.

Embodiments may include none, one, some, or all of the following features: The fluid management system includes an electromagnetic system that includes the electrode pair and the magnetic field system. The electromagnetic system includes a circuit and a winding. The circuit provides an electric voltage to the electrode pair to generate the electric field. The winding generates a magnetic field orthogonal to the electric field to move the fluid in the pumping direction. The housing comprising tubing or a chamber with a rectangular box shape. The magnetic field system may generate the magnetic field in a direction substantially parallel to the pumping direction or in a direction substantially orthogonal to the pumping direction. The irrigation pump and/or the aspiration pump may be a magnetic pump. The fluid management system includes a controller that coordinates operation of magnetic pumps.

In certain embodiments, a handpiece for an ophthalmic surgical system includes an irrigation channel, an aspiration channel, and a magnetic pump. The irrigation channel is in fluid communication with an irrigation system and carries fluid from the irrigation system. The aspiration channel is in fluid communication with an aspiration system and carries fluid toward the aspiration system. The magnetic pump moves the fluid and includes an electrode pair and a magnetic field system. The electrode pair generates an electric field about the fluid. The magnetic field system generates a magnetic field to move the fluid in a pumping direction.

Embodiments may include none, one, some, or all of the following features: The pumping direction moving the fluid from the irrigation system or moving the fluid toward the aspiration system.

In certain embodiments, a priming system for a surgical cassette of an ophthalmic surgical system includes a magnetic plug system, a fluid administration apparatus, and a magnetic field system. The magnetic plug system includes one or more magnetic plugs. The fluid administration apparatus provides fluid to the surgical cassette. Each magnetic plug is configured to be disposed within the fluid administration apparatus. The fluid administration apparatus includes a fluid administration conduit, a plug entrance, and a plug exit. The fluid administration conduit has a fluid source end that receives the fluid from a fluid source, and a surgical cassette end that provides the fluid to the surgical cassette. The plug entrance provides an entrance to the fluid administration conduit, and the plug exit provides an exit from the fluid administration conduit. The magnetic field system produces a magnetic field to move the one or more magnetic plugs in order to move the fluid from the fluid source end towards the surgical cassette end of the fluid administration conduit.

Embodiments may include none, one, some, or all of the following features: The magnetic field system includes a magnet system that has one or more magnets disposed about the fluid administration apparatus. Each magnet yields a moving magnetic field that moves a magnetic plug of the magnetic plug system. The magnet system may include a conduit magnet that moves a magnetic plug from the plug entrance towards the plug exit of the fluid administration conduit, an entrance magnet that moves a magnetic plug towards the fluid administration conduit via the plug entrance, and/or an exit magnet that moves a magnetic plug away from the fluid administration conduit via the plug exit. The magnetic field system includes a magnet system that has one or more magnets. At least one magnet has a toroid shape configured to be disposed about the fluid administration apparatus. The magnet may open to allow the magnet to be disposed about the fluid administration apparatus. The magnetic field system includes a coil system that generates the magnetic field. The coil system includes one or more electromagnetic coils disposed about the housing. The plug entrance may be plug insertion tubing or a squeeze applicator coupled to a plug insertion port. The plug exit may be plug extraction tubing coupled to a plug extraction port. The priming system includes a drain receptacle configured to collect fluid from the surgical cassette.

In certain embodiments, a method of priming a surgical cassette of an ophthalmic surgical system includes: coupling together an irrigation conduit and an aspiration conduit of the surgical cassette; coupling the surgical cassette to a surgical cassette end of a fluid administration conduit of a fluid administration apparatus of a priming system; coupling a fluid source to a fluid source end of the fluid administration conduit; inserting one or more magnetic plugs of a magnetic plug system into the fluid administration apparatus; disposing a fluid from the fluid source into the fluid administration conduit; and producing a moving magnetic field using a magnetic field system to move at least one of the magnetic plugs to move the fluid from the fluid source end towards the surgical cassette end of the fluid administration conduit in order to prime the surgical cassette.

Embodiments may include none, one, some, or all of the following features: A magnetic plug may be inserted into a plug entrance and/or a plug exit of the fluid administration apparatus.

DESCRIPTION OF EXAMPLE EMBODIMENTS

Figure 1:
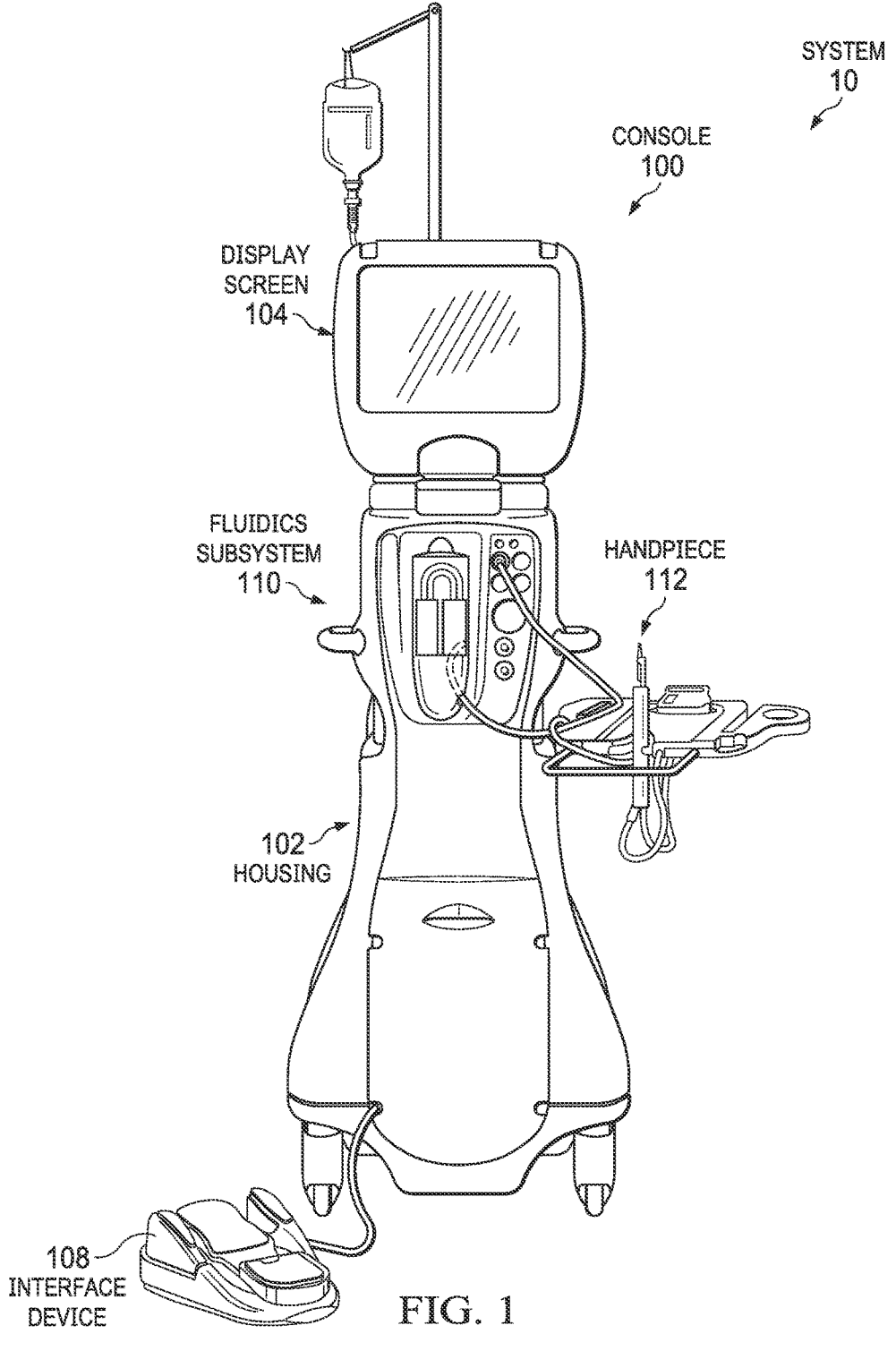
FIG. 1 illustrates an example of an ophthalmic surgical system that may be used to perform ophthalmic procedures on an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain embodiments, a fluidics system includes one or more magnetic pumps that move fluid into and out from the eye during ophthalmic surgery to maintain a target IOP of the eye. A magnetic pump utilizes a magnetic field to move (e.g., push or pull) fluid through a housing. In certain embodiments, the magnetic pump includes a magnetic plug system with one or more magnetic plugs. The magnetic field moves the plug(s), which in turn moves the fluid. In other embodiments, the magnetic field moves the fluid itself. For example, the fluid may be a superparamagnetic ferrofluid that can be moved by the magnetic field. As another, the fluid may be an electrolyte. A current is applied to the electrolyte, which allows the fluid to be moved by the magnetic field.

In certain embodiments, the magnetic field can be precisely controlled, which allows for more precise control of pumping, with minimal backlash, hysteresis, or stiction. In certain embodiments, a magnetic pump may be less expensive to make, as the materials and assembly may be less expensive. In certain embodiments, a magnetic pump may have fewer or no moving parts, so may be less susceptible to wear, fatigue, and failure, and thus more reliable.

1. Ophthalmic Surgical System and Console

FIG. 1 illustrates an example of an ophthalmic surgical system 10 that may be used to perform ophthalmic procedures on an eye, according to certain embodiments. In the illustrated example, system 10 includes a console 100 and a handpiece 112. Console 100 includes a housing 102, a display screen 104, an interface (IF) device 108 (e.g., a foot pedal), and a fluidics subsystem 110, coupled as shown and described in more detail with reference to FIG. 2.

A magnetic pump may be located at any suitable part of ophthalmic surgical system 10, e.g., at fluidics subsystem 110 and/or handpiece 112. In certain embodiments, fluidics subsystem 110 includes pumps that move fluid into and out from the eye during ophthalmic surgery to maintain a target IOP of the eye. In the embodiments, fluidics subsystem 110 includes an irrigation system and an aspiration system, both of which may be in fluid communication with handpiece 112. The irrigation system carries fluid toward handpiece 112, and includes an irrigation pump that moves the fluid toward handpiece 112. The aspiration system carries fluid away from handpiece 112, and includes an aspiration pump that moves the fluid away from handpiece 112. One or more pumps of fluidics subsystem 110 may be a magnetic pump, e.g., the irrigation pump and/or the aspiration pump may be a magnetic pump.

In certain embodiments, a magnetic pump may be incorporated with handpiece 112. In the embodiments, handpiece 112 includes an irrigation channel and an aspiration channel. The irrigation channel is in fluid communication with an irrigation system and carries fluid from the irrigation system. The aspiration channel is in fluid communication with an aspiration system and carries fluid toward the aspiration system. A magnetic pump moves the fluid in a pumping direction. The pumping direction may be from the irrigation system and/or toward the aspiration system.

Figure 2:
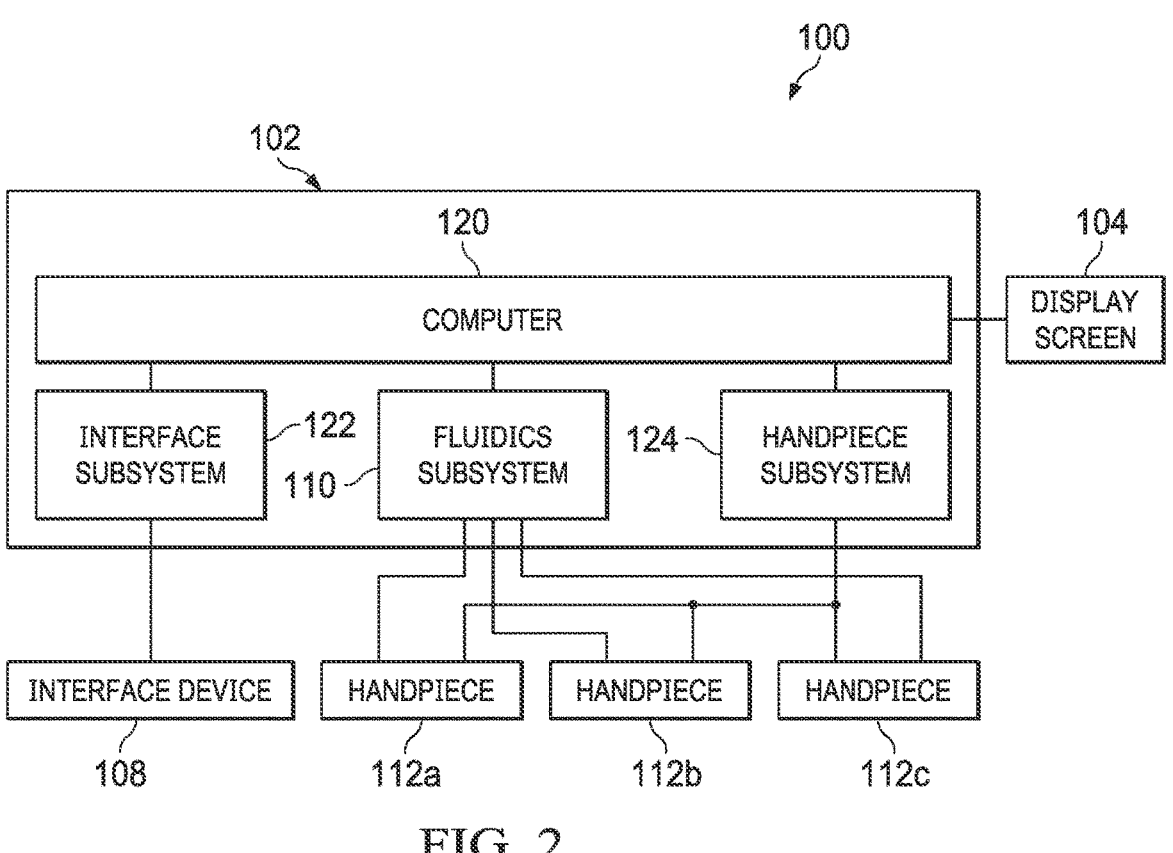
FIG. 2 illustrates an example of subsystems of console of the ophthalmic surgical system of FIG. 1, according to certain embodiments.

FIG. 2 illustrates an example of subsystems of console 100 of ophthalmic surgical system 10 of FIG. 1, according to certain embodiments. Console 100 includes housing 102, which accommodates a computer 120 (with an associated display screen 104) and subsystems 122, 110, and 124, which support interface device 108 and handpieces 112 (112*a-c*). An interface device 108 receives input to surgical system 10, sends output from system 10, and/or processes the input and/or output. Examples of an interface device 108 include a foot pedal, manual input device (e.g., a keyboard), and a display. Interface subsystem 122 receives input from and/or sends output to interface device 108.

Handpiece 112 may be any suitable ophthalmic surgical instrument, e.g., an ultrasonically-driven phacoemulsification (phaco) handpiece, a laser handpiece, an irrigating cannula, a vitrectomy handpiece, or other suitable surgical handpiece.

Fluidics subsystem 110 provides fluid control for one or more handpieces 112 (112*a-c*). For example, fluidics subsystem 110 may manage fluid for an irrigating cannula. Handpiece subsystem 124 supports one or more handpieces 112. For example, handpiece subsystem 124 may manage ultrasonic oscillation for a phaco handpiece, provide laser energy to a laser handpiece, control operation of an irrigating cannula, and/or manage features of a vitrectomy handpiece.

Computer 120 controls operation of ophthalmic surgical system 10. In certain embodiments, computer 120 includes a controller that sends instructions to components of system 10 to control system 10. A display screen 104 shows data provided by computer 120.

2. Fluidics Subsystem

Figure 3:
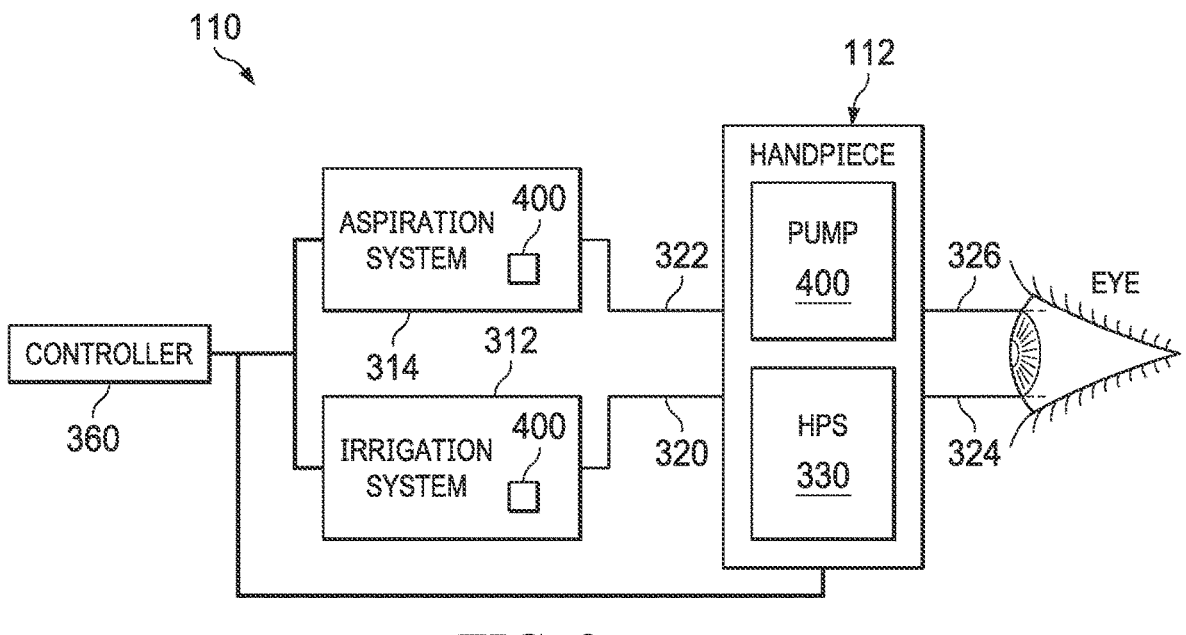
FIG. 3 illustrates an example of a fluidics subsystem that may be used with the surgical console of the ophthalmic surgical system of FIGS. 1 and 2, according to certain embodiments.

FIG. 3 illustrates an example of a fluidics subsystem 110 that may be used with surgical console 100 of ophthalmic surgical system 10 of FIGS. 1 and 2, according to certain embodiments. In general, a controller 360 (such as computer 120) controls parts of fluidics subsystem 110 to maintain a target intraocular pressure (IOP) of the eye (e.g., a value in the range of 0 to 110 millimeters of mercury (mmHg)) during a surgical procedure performed with handpiece 112. If controller 360 determines the IOP is outside of the target range, controller 360 controls fluidics subsystem 110 to bring the pressure back to the target range. For example, a post-occlusion break may create an unacceptable surge in volume demand from the eye. To mitigate the surge, the fluidics subsystem may meet the fluid demand before the volume is demanded from the eye.

In the illustrated example, fluidics subsystem 110 includes an irrigation system 312 and an aspiration system 314, which are controlled by controller 360. Irrigation system 312 and aspiration system 314 are in fluid communication with a handpiece 112. During normal operation, irrigation system 312 carries fluid toward handpiece 112, and aspiration system 314 carries fluid away from handpiece 112. The fluid is generally a biocompatible infusion fluid, e.g., a balanced salt solution (BSS). Irrigation conduit 320 provides fluid communication between irrigation system 312 and handpiece 112, and aspiration conduit 322 provides fluid communication between aspiration system 314 and handpiece 112. Parts that are in fluid communication with each other are parts for which fluid is allowed to flow between (to and/or from) the parts.

Aspiration system 314 carries fluid away from handpiece 112 by creating and maintaining a vacuum pressure (or negative pressure) in a vacuum path of an aspiration conduit 322. Vacuum pressure can be described as negative pressure. Accordingly, increasing the vacuum pressure may be described as increasing negative pressure or decreasing pressure, and decreasing the vacuum pressure may be described as decreasing negative pressure or increasing pressure. In certain embodiments, an aspiration pump of aspiration system 314 may be reversed to supply fluid to aspiration conduit 322 in order to mitigate a post-occlusion break surge.

Handpiece 112 includes an irrigation channel 324, an aspiration channel 326, and a handpiece pressure sensor (HPS) 330. Irrigation channel 324 provides fluid to the surgical site, and may be an irrigating tip or an irrigating sleeve that surrounds aspiration channel 326. Aspiration channel 326 may be a hollow needle that vibrates at a fixed frequency to break up tissue. Fluid and tissue may be aspirated through the needle. In certain embodiments, handpiece 112 may be any suitable ophthalmic surgical handpiece, e.g., an ultrasonically-driven phaco handpiece, a laser handpiece that fragments a lens to facilitate phacoemulsification, or a vitreous cutting handpiece.

HPS 330 is an irrigation pressure sensor that detects the irrigation pressure within the irrigation conduit 320. An irrigation pressure sensor may be located at any suitable location, such as any suitable location of handpiece 112 (e.g., the proximal end, the distal end, or proximate the irrigation channel 324), at any suitable location along an irrigation conduit, or at any suitable component in fluid communication with the surgical site (e.g., within in a separate tube or probe). In the illustrated example, HPS 330 is located on handpiece 112 close to the surgical site, e.g., less than 12 inches from the surgical site. The proximity to the surgical site may enable quick detection of changes in pressure (as may occur during an occlusion break) and allow for real-time surge suppression. In some examples, HPS 330 detects pressure changes within 50 milliseconds of an occlusion break, which may enable controller 360 to respond to pressure deviations before IOP is overly negatively affected.

Controller 360 is a computer that controls parts of fluidics subsystem 110, such as valves or pumps, in response to pressure changes to maintain a target pressure at the surgical site. Controller 360 may determine the IOP from a pressure associated with a surgical site of the eye, or "surgical site pressure", which may be measured at the surgical site or elsewhere. Surgical system 10 may have one or more sensors at different locations that measure the surgical site pressure. For example, a sensor may be located at or inside of the eye to directly measure the IOP of the eye. As another example, the irrigation pressure measured at an irrigation conduit and/or the aspiration pressure measured at an aspiration conduit may indicate the IOP. The surgical site pressure may not be the same as the IOP, but may correspond to the IOP in that a higher surgical site pressure indicates a higher IOP and a lower surgical site pressure indicates a lower IOP. The surgical site pressure may have a target range that corresponds to the target IOP of the eye, e.g., a value in the range of 0 to 110 mmHg (e.g., a value in the range of 10 to 30, 30 to 55, 55 to 80, and/or 80 to 100 mmHg, such as 30 to 80 mmHg). For example, the irrigation pressure may have a target range of 0 to 110 mmHg (e.g., a value in the range of 0 to 30, 30 to 70, or 70 to 110 mmHg), or the aspiration pressure may have a target range of −760 to 110 mmHg (e.g., a value in the range of −760 to −300, −300 to −100, or −100 to 110 mmHg).

Controller 360 may retrieve one or more pressure thresholds from a memory. In response to detecting that a pressure has reached a pressure threshold, controller 360 provides instructions to bring the pressure back to the target range. For example, to mitigate a post-occlusion break volume surge, a first pressure threshold may indicate when the surgical site pressure has decreased to an unacceptable threshold in response to an occlusion breakage, e.g., when an undesirable volume demand has been created. In response, controller 360 decreases the vacuum pressure in aspiration conduit 322 and/or irrigation conduit 320 to mitigate the rapid decrease of the surgical site pressure. For example, controller 360 may provide fluid to meet the undesirable volume demand to bring the surgical site pressure closer to a desirable level. The first pressure threshold may have any suitable value, e.g., a value in the range of 0 to 207 mmHg (e.g., a value in the range of 0 to 35, 35 to 100, or 100 to 207 mmHg).

A second pressure threshold may indicate when the surgical site pressure is at an acceptable threshold, indicating the surgical site pressure has recovered. In response, controller 360 ceases decreasing the vacuum pressure in the aspiration conduit 322 and/or irrigation conduit 320. The second pressure threshold may have any suitable value, e.g., a value in the range of −760 to 207 mmHg (e.g., a value in the range of −760 to −600, −600 to −400, −400 to −200, −200 to 0, or 0 to 207 mmHg). In some embodiments, the second pressure threshold may be selected such that controller 360 stops decreasing the vacuum pressure before the target IOP range is reached, since the vacuum pressure typically continues to decrease for a short while after controller 360 acts to stop the decrease.

While the above example uses a first pressure threshold defined in terms of an irrigation pressure and a second pressure threshold defined in terms of an aspiration pressure, the first and second thresholds may be defined in terms of use suitable type of pressure (e.g., aspiration pressure, an irrigation pressure, or an intraocular pressure) from any suitable sensors that indicate the pressure at the surgical site. In addition, the first and/or second thresholds can be defined in terms of the same or different types of pressure, e.g., both thresholds could be defined in terms of an aspiration pressure.

3. Magnetic Pumps

Fluidics subsystem 110 and/or handpiece 112 may include one or more magnetic pumps 400. A magnetic pump 400 utilizes a magnetic field to move fluid through a housing. The magnetic field is generated by any suitable magnetic field system. In certain embodiments, the magnetic field system includes a coil system comprising one or more electromagnetic coils disposed about the housing. For example, a coil may be wrapped around at least a portion of the housing. An electric current is passed through the coil(s) to generate the magnetic field. In other embodiments, the magnetic field system includes a magnet system comprising one or more magnets disposed about the housing. For example, a magnet may encircle at least a portion of the housing. The magnets generate the magnetic field.

The magnetic field moves the fluid in any suitable manner. In certain embodiments, the magnetic pump includes a magnetic plug system with one or more magnetic plugs. The magnetic field moves the plug(s), which in turn moves (e.g., pushes or pulls) the fluid. A magnetic plug may be any suitable magnetically influenced object, which may comprise, e.g., a magnetic material such as a ferromagnetic material. A magnetic plug may have any suitable shape or size that moves the fluid through the housing. For example, the plug may have an outer perimeter (defined by an outer surface) that is the same as or smaller than (e.g., 80 to 100% the size of) the inner perimeter (defined by an inner surface) of the housing.

In other embodiments, the magnetic field moves the fluid itself. In some cases, the fluid may be a superparamagnetic ferrofluid that is moved by the magnetic field. In other cases, the fluid may be an electrolyte. A current is passed through the fluid, and the magnetic field system generates a magnetic field orthogonal to the current. The orthogonal magnetic field, electric field, and relative motion of ions results in a Lorentz force that moves the fluid.

The housing holds the fluid to allow the magnetic field to move the fluid in the pumping direction. The housing may have any suitable shape or size. In certain embodiments, the housing has a cylindrical shape. Examples include tubing or a cylindrical chamber. In certain embodiments, the housing has a rectangular shape. Examples include a chamber with a rectangular box shape.

A magnetic pump 400 may be used in irrigation system 312, aspiration system 314, and/or handpiece 112. For example, a magnetic irrigation pump 400 may move the fluid toward handpiece 112, and/or a magnetic aspiration pump may move the fluid away from handpiece 112. As another example, a magnetic pump may be coupled to or incorporated within handpiece 112, which may improve response time. The handpiece pump may move the fluid from irrigation system 312 and/or toward aspiration system 314. In certain embodiments, magnetic pumps 400 of the same type (or different types) may be used in irrigation and aspiration systems 312, 314, and their operation may be coordinated, e.g., by controller 360, to achieve or maintain a target IOP.

In certain embodiments, a controller (e.g., controller 360) controls one or more magnetic pumps 400. The controller may control the pump(s) to maintain a target pressure at the surgical site in response to pressure changes, as described previously. For example, in response to detecting that a pressure has reached a pressure threshold, the controller instructs the pump(s) 400 to bring the pressure back to the target range. In some cases, the controller may synchronize the operation of magnetic irrigation and aspiration pumps to adjust the pressure. In these cases, magnetic pumps of the same type may more readily allow for electric synchronization of the pumps. In some cases, the controller may conduct a 4-quadrant operation to instruct magnetic irrigation and aspiration pumps to work in phase (irrigating or aspirating together) to manage, e.g., an occlusion break.

In certain embodiments, a magnetic pump 400 may be utilized in a priming system for a surgical cassette when the cassette is outside of the console. The priming system includes a fluid administration conduit that receives fluid from a fluid source and provides the fluid to the surgical cassette. Magnetic plugs are disposed within the conduit. Magnets produce a magnetic field that moves the magnetic plugs in order to move the fluid from the fluid source towards the surgical cassette. This movement provides fluid to the surgical cassette to prime the cassette.

In certain embodiments, a magnetic pump 400 may provide more precise control of pumping. For example, the magnetic field can provide pumping forces in a wide range of frequencies (starting as low as, e.g., 0 Hz), allowing for precise control of starting and stopping the plug. Moreover, there is minimal backlash, hysteresis, or stiction. In addition, the magnetic forces are linearly scaled with flow sensing voltages, so the magnetic field can be readily adjusted in response to flow changes. In certain embodiments, a magnetic pump 400 may be less expensive to make, as the materials and assembly may be less expensive and certain components may not be required. For example, a magnetic pump 400 does not require valves to stop the fluid flow, as the flow is stopped by stalling the magnetic field. In certain embodiments, a magnetic pump 400 may have no or fewer moving parts, so may be less susceptible to wear, fatigue, and failure, and thus more reliable.

Examples of types of magnetic pumps 400 are described in more detail with reference to FIGS. 4 through 11.

3.1 Magnetic Plug Pumps

Figures 4, 5:
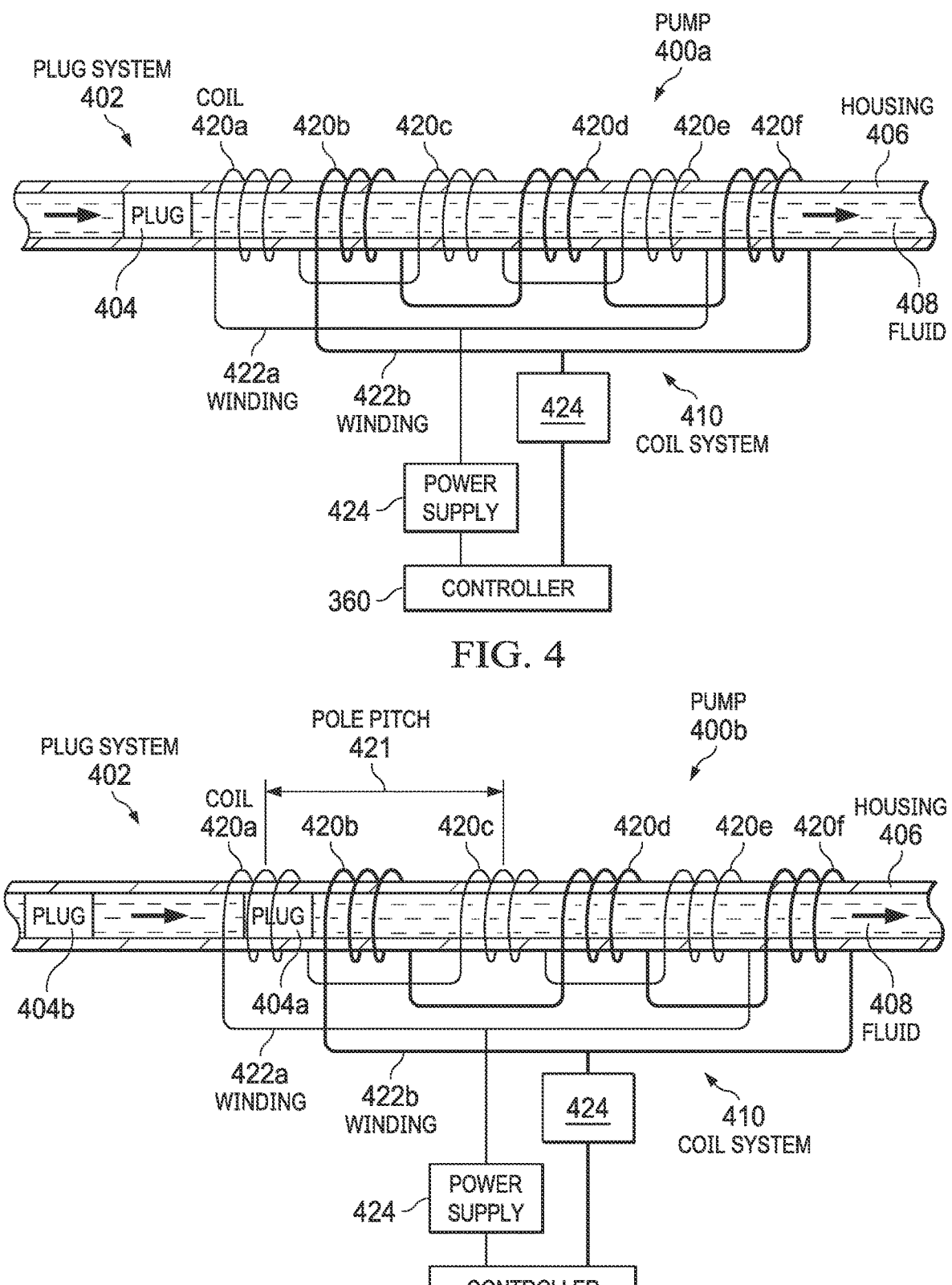
FIG. 4 illustrates an example of a magnetic pump with one plug.
FIG. 5 illustrates an example of a magnetic pump with a plurality of plugs.

FIGS. 4 though 9 illustrate examples of magnetic pumps 400 (400a-400e) that include a magnetic plug system 402 comprising one or more magnetic plugs 404 (404a-404b) disposed within a housing 406 that contains fluid 408. A magnetic field system (e.g., a coil system or magnet system) generates a magnetic field. The magnetic field moves the plug(s) 404, which in turn move fluid 406 in a pumping direction.

Any suitable number of plugs 404 may be used. In general, multiple plugs 404 multiply the force applied to move fluid 408. For example, a first plug pushes the fluid in front of first plug. A second plug pushes the fluid between the first and second plugs, the first plug, and the fluid in front of first plug, and so on.

3.1.1 Coil Systems

FIGS. 4 though 8 illustrate examples of magnetic pumps 400 (400a-400d) with a magnetic field system comprising a coil system 410. In the examples, coil system 410 comprises one or more electromagnetic coils 420 (420a-420f) and a power supply 424. Coils 420 are disposed about housing 406. A winding 422 (422a-422b) wraps one or more turns around housing 406 to form an electromagnetic coil 420. Winding 422 comprises an electrical conductor (e.g., a wire). When an electric current is passed through winding 422 by, e.g., power supply 424, coil 420 generates a magnetic field. The magnetic field pulls a plug 404 to the midpoint of coil 420, which in turn moves fluid 408. In certain embodiments, a computer such as controller 360 may instruct power supply 424 to turn on and turn off the current in a coil 420.

Coil system 410 may be designed in accordance with the surgical length of fluid, i.e., the length of fluid 408 (measured in the pumping direction) that travels through housing 406 during a procedure. The surgical length may be determined in accordance with the amount of fluid 408 estimated to be used for the procedure, and may include an optional additional amount to be used in atypical (e.g., emergency) situations. The surgical length may take into account whether housing 406 is refilled with fluid 408 during the procedure. For example, the surgical length may be shorter for a housing 406 that is refilled than a housing 406 that is not.

Coil system 410 may have any suitable number of coils. In certain embodiments, coil system 410 includes a first coil configured to generate the magnetic field to move the plug. In other embodiments, coil system 410 includes the first coil and a second coil successive to the first coil. The second coil generates the magnetic field to continue to move the plug in the pumping direction. Other embodiments may comprise more than two coils. In certain embodiments, the number of coils 420 may be selected in accordance with the surgical length of fluid. The number of coils 420 may be selected to allow coils 420 to move one or more magnetic plugs 404 to move fluid 408 through the surgical length. In some cases, the coil system 410 and/or plugs 404 may be positioned such that the plug 404 closest to the pump outlet (or inlet) moves through the surgical length.

Coils 420 may be distributed along housing 406 in any suitable manner. In certain embodiments, the coil pitch (i.e., the distance between the midpoints of two successive coils 420) may be the same (or may be different) between successive coils 420 of a coil system 410. In certain embodiments, the length of the coil pitch and/or the length of plug 404 may be selected to allow a plug 404 at a current coil 420 to be pulled by the magnetic field of the next coil 420. For example, the plug may have a length of 1.1 to 1.8 (such as approximately 1.5) times the coil pitch of the coils.

Any suitable number of windings 422 may be used to form coils 420 of coil system 410. In certain embodiments, coils 420 are formed by a multiple (at least two) phase winding. For example, as shown in FIGS. 4 and 5, a two-phase winding is used. Winding 422a forms coils 420a, 420c, 420e, and winding 422b forms coils 420b, 420d, 420f. A winding 422 may have any suitable number of turns to form a coil 420. The number of turns may be selected in accordance with the strength of the magnetic field required to move plug 404. In general, the more turns yields greater magnetic strength. A winding 422 may have any suitable size and shape that conform to wrap around housing 406. For example, if housing 406 is a cylinder, the winding may have a helix shape that wraps around the cylinder. As another example, if housing 406 is a rectangular box, the winding may have a helix-type shape that wraps around the box, where each turn traces a rectangle.

In an example of operation, a current is switched on and off through coils 420 to create magnetic fields that move plug(s) 404 in the pumping direction. A magnetic field may be generated in each coil 420 of a sequence of coils 420 such that it appears to plug 404 that a magnetic field is moving through the sequence of coils 420. In embodiments with multi-phase windings, phase-shifted currents may create the moving magnetic field. In certain embodiments, power supply 424 may switch the current on and off by, e.g., sold state switching. In certain embodiments, a computer such as controller 360 may instruct power supply 424 to control currents in various sections of coil 420 by working in switched mode or linear mode as applicable.

FIGS. 4 and 5 illustrate examples of magnetic pumps 400 (400a, 400b) with magnetic plugs 404, a coil system 410, and a cylindrical housing 406. Cylindrical housing 406 may be, e.g., surgical tubing.

FIG. 4 illustrates a magnetic pump 400a with one plug 404. In an example of operation, a magnetic field is switched on and off by coils 420 to move plug 404 from coil 420a to coil 420f. For example, in a 2-phase winding, voltages are applied in 90° phase-shifted patterns. When a phase reaches a half-way point, the next phase is turned on, so a plug 404 can continue to move.

In the illustrated example, at a first phase, a current is passed through first coil 420a via winding 422a. First coil 420a generates a first magnetic field that pulls plug 404 to the midpoint of first coil 420a, which moves fluid 408. Halfway through the first phase, a current is already passing through second coil 420b via winding 422b to generate a second magnetic field of a second phase. The current in first coil 420a is ceased, which stops the first magnetic field. The second magnetic field pulls plug 404 to the midpoint of second coil 420b, which moves fluid 408. A magnetic field is generated and ceased by the rest of the coils 420 to move plug to coil 420f.

FIG. 5 illustrates a magnetic pump 400b with a plurality of plugs 404 (404a, 404b). Each plug 404 is a pole pitch distance 421 away from the next plug 404. The pole pitch 421 is the distance between coils 420 of the same winding 422. In an example of operation, a magnetic field is switched on and off by coils 420 to move first plug 404a to first coil 420a, then to second coil 420b, and then to third coil 420c as described with reference to FIG. 4. As first plug 404a reaches third coil 420c, second plug 404b reaches first coil 420a via influence of the magnetic field of first coil 420a. Magnetic fields are switched on and off by the remaining coils 420 to move plugs 404 to coil 420f.

Figure 6:
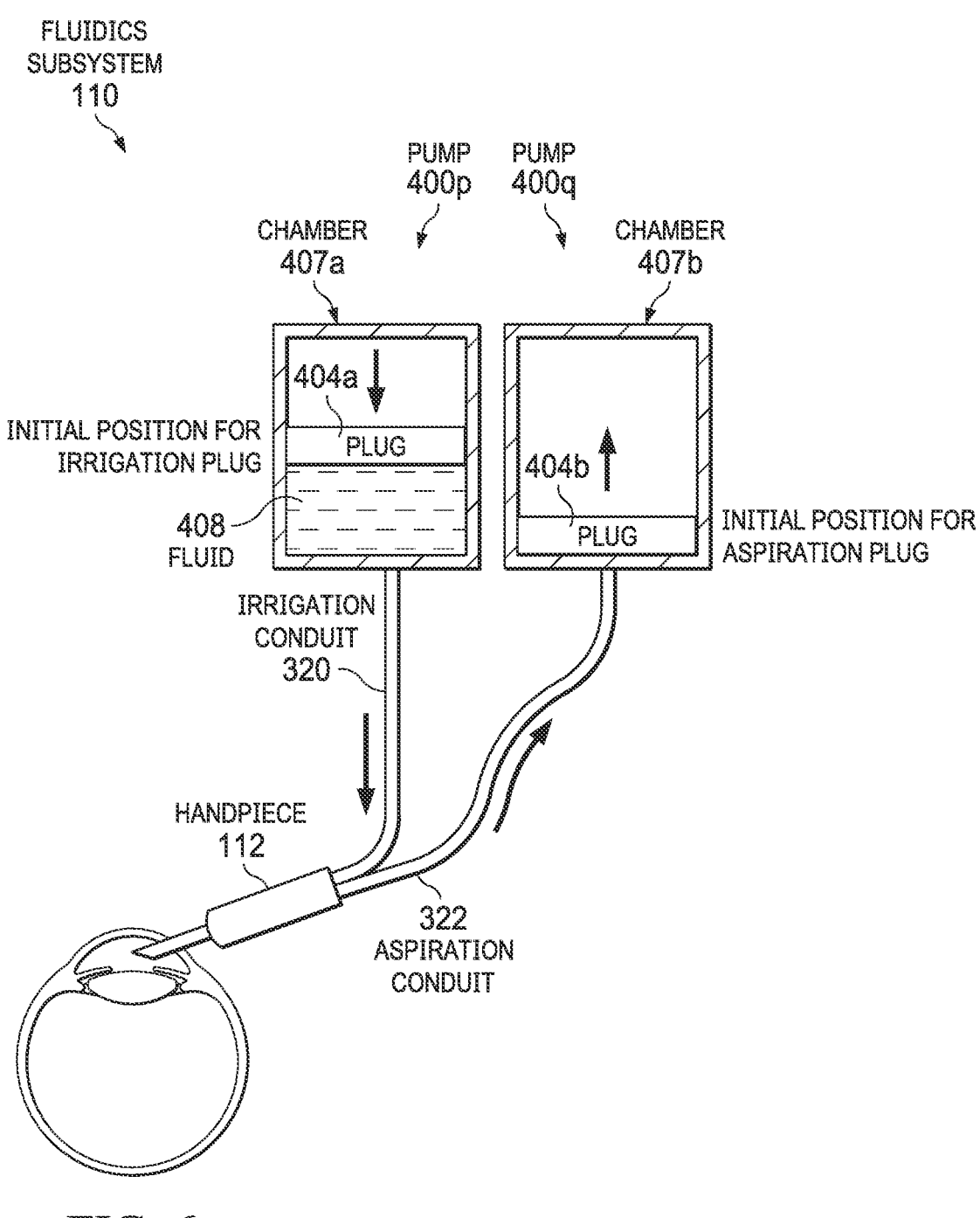
FIG. 6 illustrates a fluidics subsystem that includes examples of magnetic pumps for irrigation and/or aspiration.

FIG. 6 illustrates a fluidics subsystem 110 that includes examples of magnetic pumps 400 (400p, 400q) for irrigation and/or aspiration. In the example, fluidics subsystem 110 includes irrigation magnetic pump 400p, aspiration magnetic pump 400q, irrigation conduit 320, aspiration conduit 322, and handpiece 112 coupled as shown.

In the example, the housings of pumps 400 are chambers 407 (407a, 407b). A chamber 407 may have a size and shape that can accommodate fluid 408 for the procedure. In certain embodiments, chamber 407 may be thin in one dimension in order to apply a magnetic field of suitable strength. A magnetic plug 404 (404a, 404b) may be the same size and shape as or smaller than the inner surface of chamber 407 to move through chamber 407.

Irrigation magnetic pump 400p pumps fluid 408 towards irrigation conduit 320. More specifically, a magnetic field system (not shown) of irrigation magnetic pump 400p generates a magnetic field that moves plug 404a towards an outlet of chamber 407a to push fluid 408 through the outlet, which leads to irrigation conduit 320. Aspiration magnetic pump 400q pumps fluid 408 from aspiration conduit 322. More specifically, a magnetic field system (not shown) of aspiration magnetic pump 400q generates a magnetic field that moves plug 404a away from an inlet of chamber 407b to pull fluid 408 from aspiration conduit 322 through the inlet.

Figure 7:
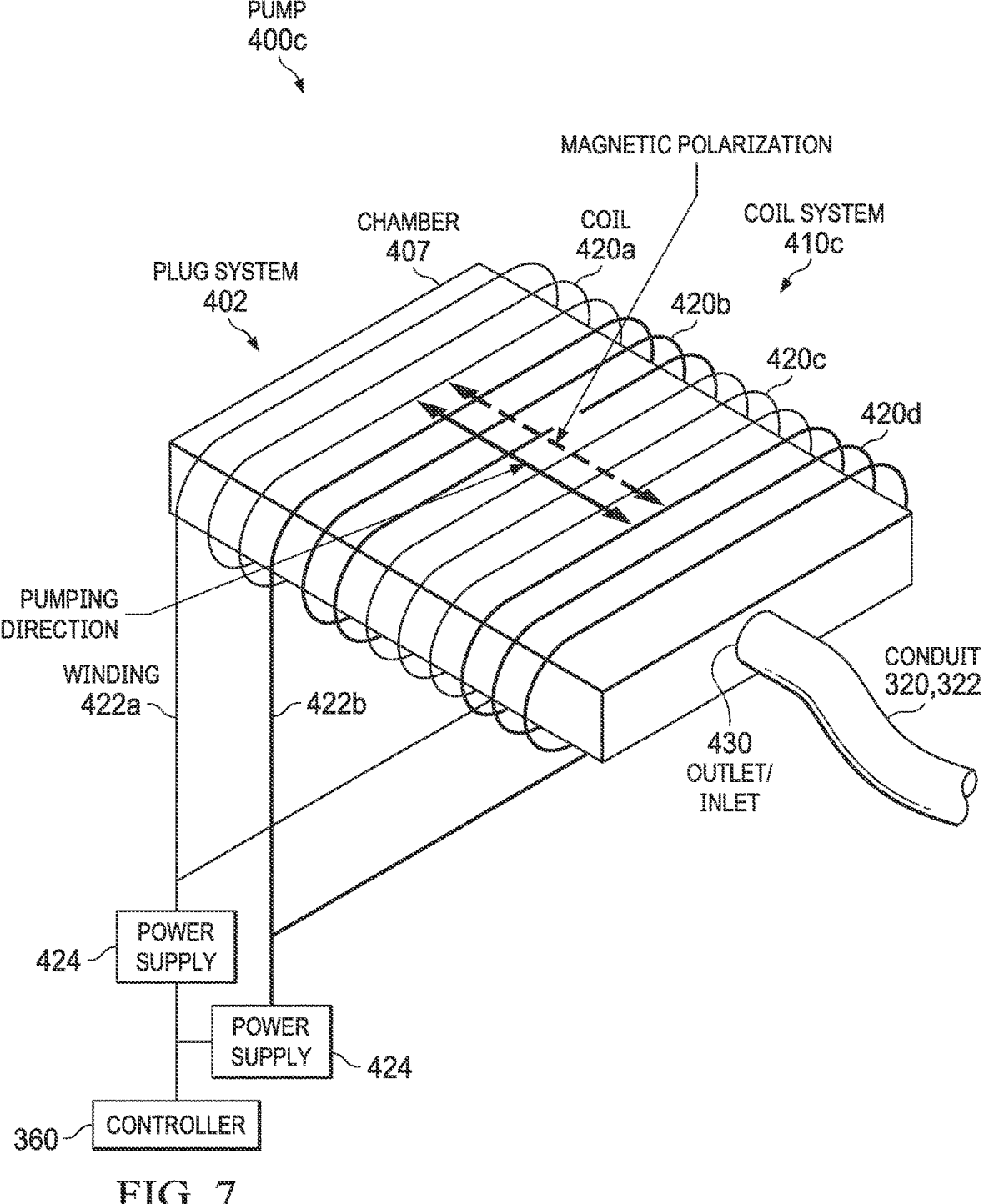
FIG. 7 illustrates an example of a magnetic pump with a coil system that generates a magnetic field with a polarization parallel to the pumping direction.
Figure 8:
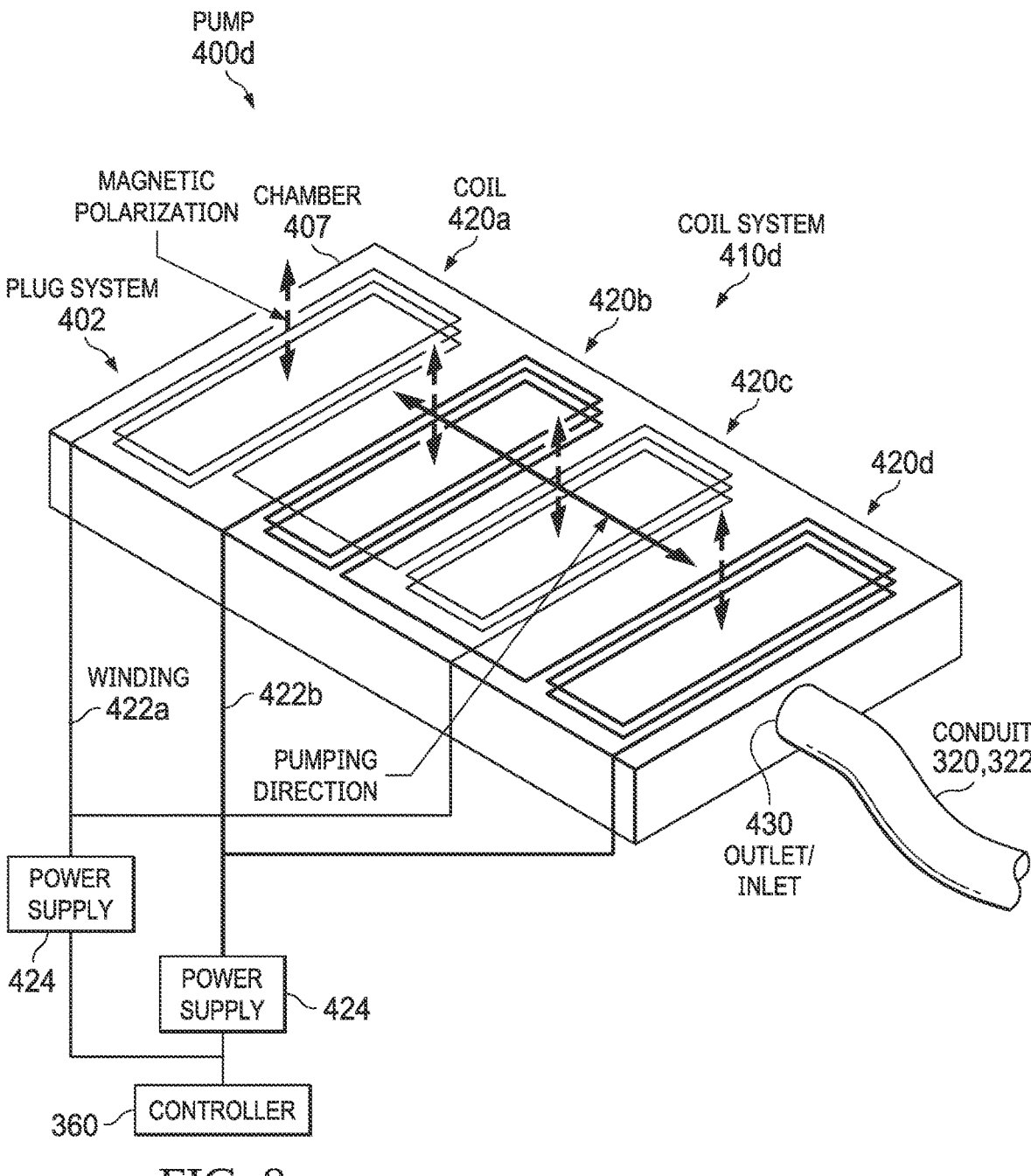
FIG. 8 illustrates an example of a magnetic pump with a coil system that generates a magnetic field with polarization orthogonal to the pumping direction.

FIGS. 7 and 8 illustrate examples of magnetic pumps 400 (400c, 400d) with a magnetic field system comprising a coil system 410 (410c, 410d). In the examples, magnetic pumps 400 (400c, 400d) comprises the magnetic field system, a chamber 407, and a magnetic plug system 402 (disposed within chamber 407), coupled as shown. The magnetic field system comprises a coil system 410 (410c, 410d) and power supplies 424. Coil system 410 includes windings 422 (422a-422b) that form coils 420 (420a-420d) disposed about chamber 407. In certain embodiments, a computer such as controller 360 may instruct power supply 424 to turn on and turn off the current in a coil 420. Chamber 407 has an outlet/inlet 430 coupled to a conduit 320, 322. For example, if magnetic pump 400 is an irrigation magnetic pump 400p, outlet/inlet 430 is an outlet coupled to irrigation conduit 320. If magnetic pump 400 is an aspiration magnetic pump 400q, outlet/inlet 430 is an inlet coupled to aspiration conduit 322.

FIG. 7 illustrates a magnetic pump 400c that includes a coil system 410c that generates a magnetic field with a polarization parallel to the pumping direction. Coil system 410c moves magnetic plug system 402 through chamber 407 in a manner similar to that described with reference to FIGS. 4 and 5. For example, if magnetic pump 400c is an irrigation pump, a magnetic field is switched on and off by coils 420 to move plug(s) from coil 420a to coil 420d to move fluid 408 towards outlet 430. If magnetic pump 400c is an aspiration pump, a magnetic field is switched on and off by coils 420 to move plug(s) from coil 420d to coil 420a to move fluid 408 from inlet 430.

In an example of operation of an irrigation magnetic pump 400c, a current is passed through first coil 420a to generate a magnetic field that pulls a first plug to the midpoint of first coil 420a, which moves fluid 408. While a first current in first coil 420a is ramped down, a second current is ramped up through second coil 420b to generate a magnetic field that pulls the first plug to the midpoint of second coil 420b, which moves fluid 408. If there is a second plug, as the first plug reaches second coil 420b, the second plug reaches first coil 420a via influence of the magnetic field of first coil 420a, which moves fluid 408. The magnetic field is switched on and off to move plug(s) to fourth coil 420d.

FIG. 8 illustrates a magnetic pump 400c that includes a coil system 410d that generates a magnetic field with polarization orthogonal to the pumping direction. In certain embodiments, a magnetic yoke may be used to increase the magnetic field strength. Yokes are suitably shaped, high-permeability ferromagnetic solids that are used to fill the magnetic flux path, except the airgaps. Coil system 410d moves magnetic plug system 402 through chamber 407 in a manner similar to that described with reference to FIG. 7.

3.1.2 Magnet Systems

Figure 9:
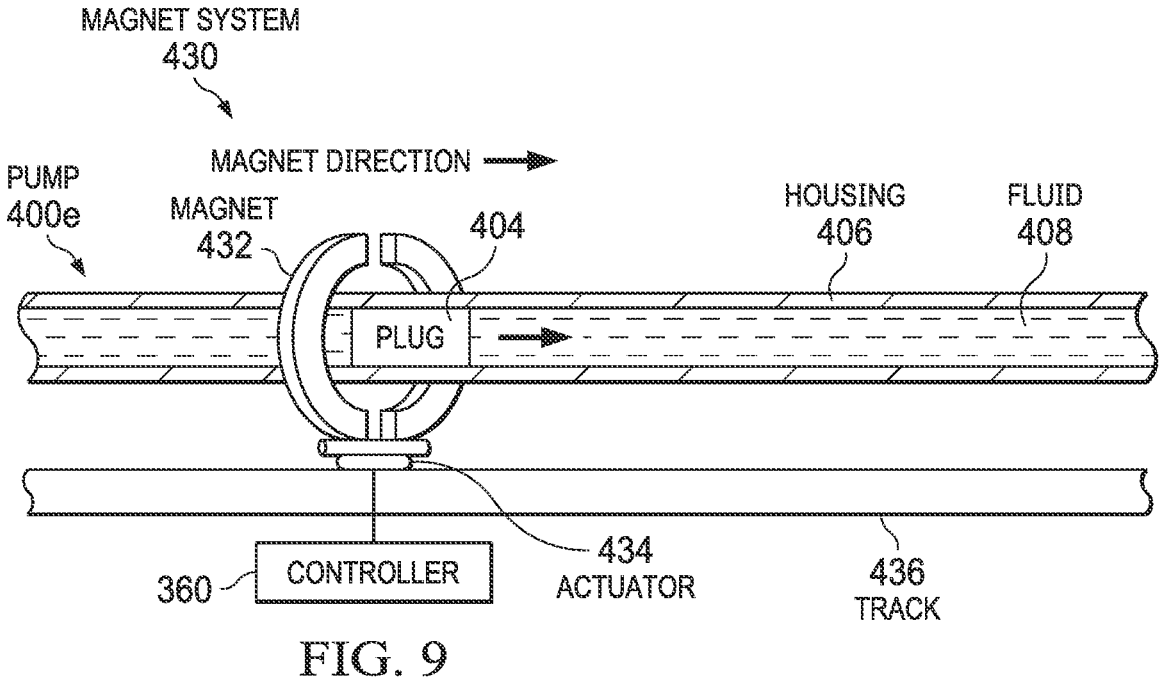
FIG. 9 illustrates an example of a magnetic pump with a magnetic field system comprising a magnet system.

FIG. 9 illustrates an example of a magnetic pump 400 (400e) with a magnetic field system comprising a magnet system 430. In the example, magnet system 430 includes a magnet 432, an actuator 434 (which may be coupled to controller 360), and a track 436, coupled as shown. Magnet 432 generates a magnetic field that attracts plug 404. Actuator 434 controllably closes the air gaps built into magnet 432 and moves magnet 432 to move plug 404, which moves fluid 408 within housing 406 in the pumping direction. In certain embodiments, a computer such as controller 360 may instruct magnet system 430 to move magnet 432.

3.2 Ferrofluid Pumps

Figure 10:
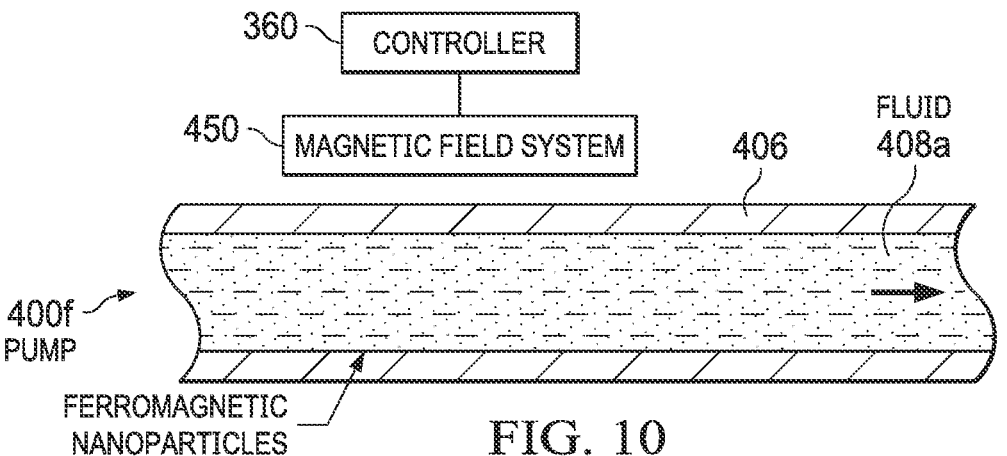
FIG. 10 illustrates an example of a magnetic pump that moves a ferrofluid, according to certain embodiments.

FIG. 10 illustrates an example of a magnetic pump 400 (400f) that moves a fluid 408 comprising a ferrofluid 408a, according to certain embodiments. Ferrofluid 408a is a superparamagnetic fluid that is attracted by magnetic poles. Accordingly, a magnetic field may move ferrofluid 408a in manners as described above. A ferrofluid 408a typically comprises magnetic solids, a surfactant that inhibits clumping of the solids, and a carrier fluid. By volume, a typical ferrofluid may be approximately 3 to 10% (e.g., 5%) magnetic solids, 5 to 15% (e.g., 10%) surfactant, and 80 to 90% (e.g., 85%) carrier fluid, by volume. Ferrofluid 408a may be any suitable ferrofluid, e.g., an infusion fluid comprising ferromagnetic nanoparticles.

In the example, pump 400f includes a housing 406 and a magnetic field system 450, coupled as shown. In certain embodiments, a computer such as controller 360 may instruct magnetic field system 450 to generate a magnetic field. In an example of operation, magnetic field system 450 generates a magnetic field that moves ferrofluid 408a through housing 406 in the pumping direction. The magnetic field may exert a continuous push/pull action on ferrofluid 408a.

Any suitable magnetic field system 450 may be used. In certain embodiments, magnetic field system 450 may comprise a coil system, such as a multi-phase (e.g., a two-phase) coil system. Pump 400f may be sufficiently small to attach to or incorporate into a handpiece 112.

3.3 Magneto Hydro Dynamic (MHD) Pumps

Figure 11:
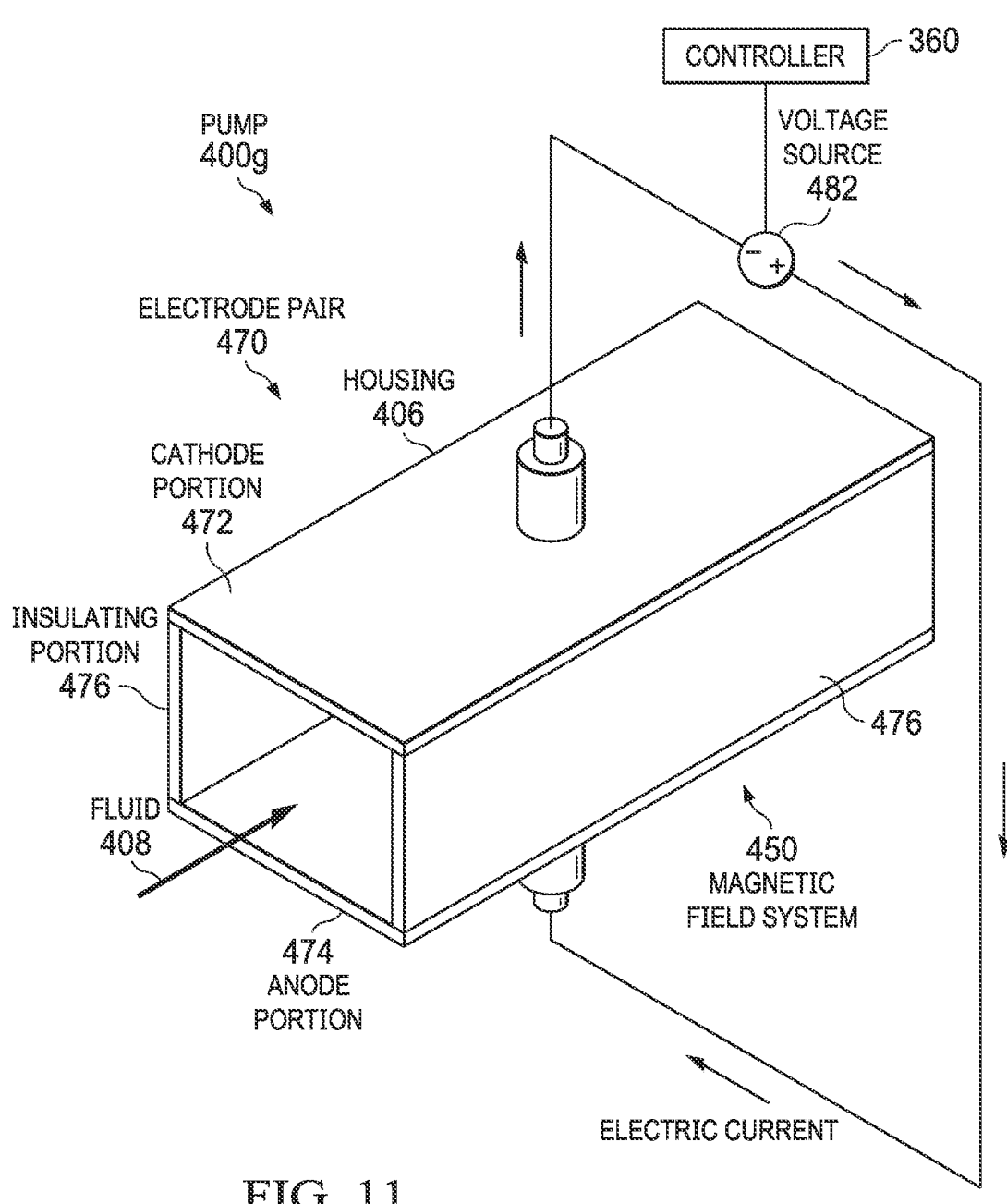
FIG. 11 illustrates an example of a magnetic pump comprising a Magneto Hydro Dynamic (MHD) pump, according to certain embodiments.

FIG. 11 illustrates an example of a magnetic pump 400 (400g) comprising a Magneto Hydro Dynamic (MHD) pump that moves fluid 408 comprising an electrically conducting fluid, e.g., an electrolyte such as a balanced salt solution (BSS), according to certain embodiments. In the example, magnetic pump 400g includes a housing 406, an electrode pair 470 (with cathode portion 472 and anode portion 474), and a magnetic field system 450. Housing 406 comprises cathode portion 472, anode portion 474, and insulating portions 476. Magnetic field system 450 may include electromagnets, permanent magnets, or both. In certain embodiments, a computer such as controller 360 may instruct magnetic field system 450 to generate the magnetic field.

In an example of operation, a voltage source 482 applies a voltage across through electrode pair 470 to establish a current (e.g., a unidirectional current) through fluid 408. A magnetic field is generated orthogonal to the current. The combination of the orthogonal magnetic field, electric field, and relative motion of ions results in a Lorentz force with direction defined by the cross product of current and magnetic field vectors. The force moves fluid 408 through housing 406 in the pumping direction.

In certain embodiments, pump 400g may be sufficiently small to be attached to or integrated with a handpiece 112. In certain embodiments, pump 400g may be used with housing 406 comprising circular tubing with a diameter greater than 100 μm.

4. Priming System

In certain embodiments, a magnetic pump may be utilized in a priming system for a surgical cassette. The priming system primes the surgical cassette when the cassette is outside of the console, allowing for more efficient priming of the cassette.

Figure 12:
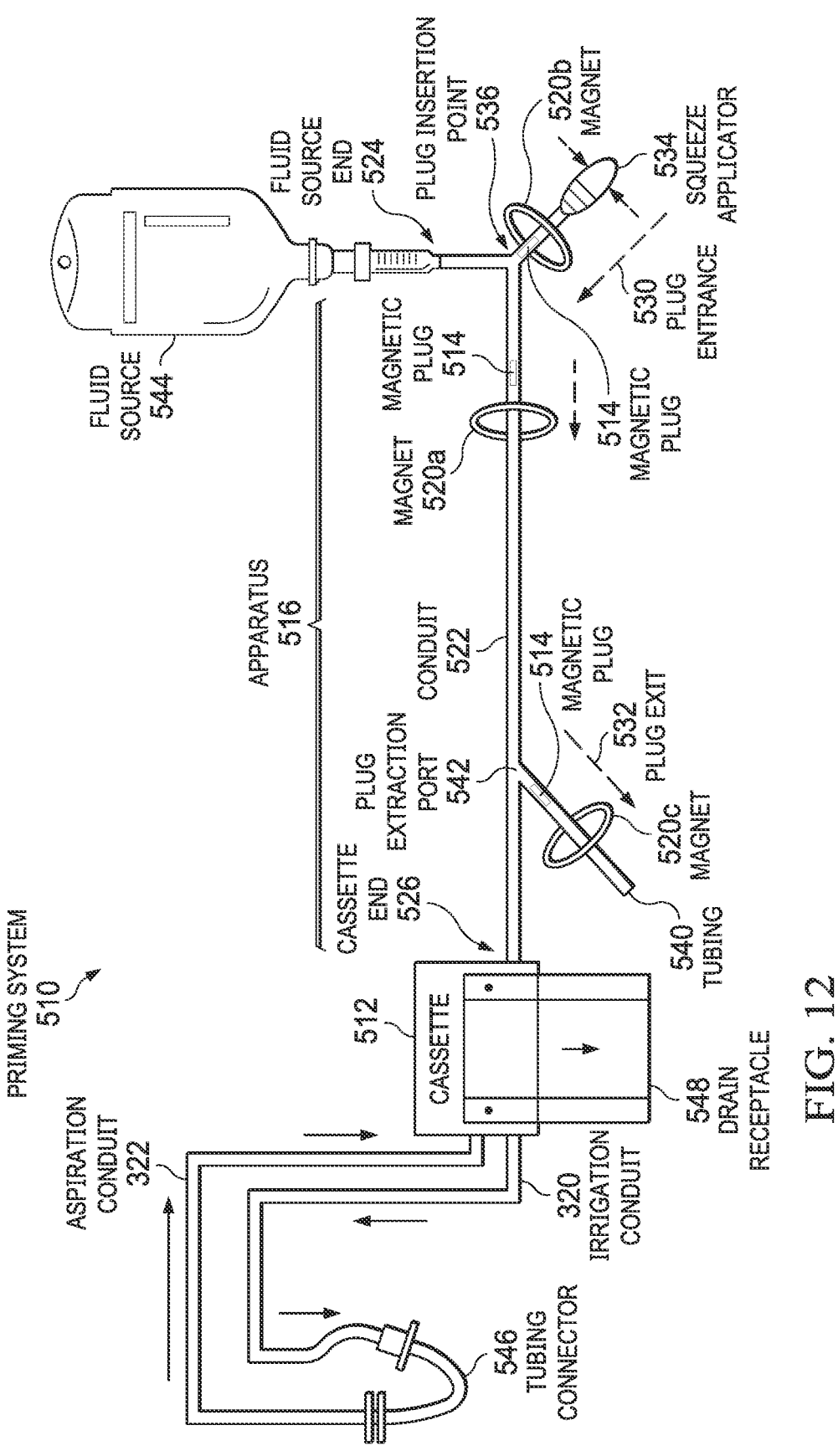
FIG. 12 illustrates an example of a priming system that may be used to prime a surgical cassette, according to certain embodiments.

FIG. 12 illustrates an example of a priming system 510 that may be used to prime a surgical cassette 512, according to certain embodiments. In certain embodiments, surgical cassette 512 may be inserted into a surgical console of an ophthalmic surgical system. Surgical cassette 512 may include a fluidics subsystem that moves fluid into and out from an eye during surgery to maintain a target IOP of the eye. Priming system 510 primes surgical cassette 512 by filling surgical cassette 512 with fluid used during surgery, e.g., BSS. Priming system 510 primes surgical cassette 512 independent of the surgical console, such that surgical cassette 512 can be primed prior to surgery without using the surgical console.

As an overview, in the example, priming system 510 includes a magnetic plug system with magnetic plugs 514, a fluid administration apparatus 516, and a magnet system with magnets 520, coupled as shown. Fluid administration apparatus 516 includes a fluid administration conduit 522 (with a fluid source end 524 and a surgical cassette end 526), a plug entrance 530, and a plug exit 532, arranged as shown. Plug entrance 530 includes a squeeze applicator 534 coupled to a plug insertion port 536, and plug exit 532 includes plug extraction tubing 540 coupled to a plug extraction port 542. To perform the priming procedure (described in more detail with reference to FIG. 14), priming system 510 is coupled to a fluid source 544 and surgical cassette 512 as shown. A tubing connector 546 couples together irrigation conduit 320 and aspiration conduit 322 of surgical cassette 512. A drain receptacle 548 is coupled to surgical cassette 512.

In more detail, in the example, a magnetic plug 514 is configured to be disposed within fluid administration apparatus 516. Magnetic plugs 514 may be substantially similar to the magnetic plugs described herein. Fluid administration apparatus 516 of priming system 510 provides fluid from fluid source 544 to surgical cassette 512. Fluid administration conduit 522 of apparatus 516 may be any suitable conduit for conveying fluid, e.g., a cylindrical conduit such as surgical tubing. Fluid source end 524 of conduit 522 couples to and receives fluid from fluid source 544 via any suitable connection, and surgical cassette end 526 couples to and provides fluid to surgical cassette 512 via any suitable connection.

Plug entrance 530 provides an entrance where a magnetic plug 514 can enter into fluid administration conduit 522. Plug insertion port 536 of plug entrance 530 is an opening that allows a magnetic plug 514 to enter conduit 522. In the example, squeeze applicator 534 is coupled to a plug insertion port 536. Squeeze applicator 534 may hold one or more magnetic plugs 514 and may be squeezed to push a magnetic plug 514 through plug entrance 530 into conduit 522. In other examples, squeeze applicator 534 may be replaced by another suitable conveyance, e.g., tubing, that performs similar operations.

Plug exit 532 provides an exit where a magnetic plug 514 can exit fluid administration conduit 522. Plug extraction port 542 of plug exit 532 is an opening that allows a magnetic plug 514 to exit conduit 522. Plug extraction tubing 540 may hold one or more magnetic plugs 514.

Plug entrance 530 and plug exit 532 may be separated by any suitable distance, e.g., 20 cm to 200 cm. The distance may be selected such that a suitable number of columns of fluid contained by conduit 522 between entrance 530 and exit 532 may fill cassette 512, e.g., 1 to 5 columns of fluid. In certain embodiments, plug entrance 530 and plug exit 532 may be coupled with a connector (not shown) such that a magnetic plug 514 that exits plug exit 532 may be readily transported to plug entrance 530 via the connector.

In certain embodiments, magnets 520 (520a to 520c) of the magnetic field system produce a magnetic field that moves magnetic plugs 514 in order to move the fluid from fluid source end 524 towards surgical cassette end 526 of fluid administration conduit 522. A magnet 520 may move a plug 514 by moving to create a moving magnetic field that the plug 514 is attracted to and follows. The magnet 520 may be moved in any suitable manner, e.g., manually by hand or by a motor connected to a track. A magnet 520 may secure a plug 514 at a location by attracting the plug 514 at the location and then remaining at the location.

One or more magnets 520 may be disposed about fluid administration apparatus 516 in any suitable manner. In the illustrated example, a conduit magnet 520a moves a magnetic plug 514 from plug entrance 530 towards plug exit 532. An entrance magnet 520b moves a magnetic plug 514 towards fluid administration conduit 522 via plug entrance 530. An exit magnet 520c moves a magnetic plug 514 away from fluid administration conduit 522 via plug exit 532. In other examples, mechanical forces (such as manual manipulation) at plug entrance 530 and/or plug exit 532 may move the magnetic plug 514 instead of entrance magnet 520b and/or exit magnet 520c.

In other embodiments, the magnetic field system comprises a coil system configured to generate a magnetic field. The coil system may include electromagnetic coils disposed about conduits and tubing of priming system 510. The coil system may be substantially similar to the coil systems described herein.

Fluid source 544 provides the fluid used in surgery (e.g., BSS) to priming system 510. Tubing connector 546 couples together irrigation conduit 320 and aspiration conduit 322 of surgical cassette 512. Drain receptacle 548 collects fluid from surgical cassette 512.

Figure 13:
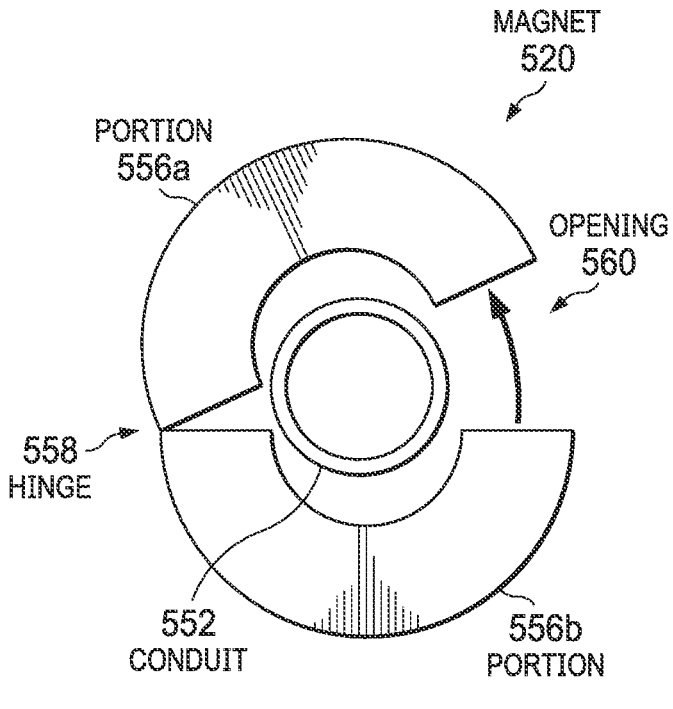
FIG. 13 illustrates an example of a magnet that may be used with the priming system of FIG. 12.

FIG. 13 illustrates an example of a magnet 520 that may be used with priming system 510 of FIG. 12. Any suitable magnet 520 that creates a magnetic field that can move a magnetic plug 514 within fluid administration apparatus 516 may be used. In the illustrated example, magnet 520 is a toroidal magnet with a toroid shape that can be disposed around a conduit 552. Conduit 552 may be any suitable conduit, e.g., tubing. The inner diameter of toroidal magnet 520 may be the same as or slightly larger than the outer diameter of conduit 552. Magnet 520 may be separated (e.g., manually) into portions 556 (556a and 556b) attached by a hinge 558. The separation creates an opening 560 that allows magnet 520 to be disposed around conduit 552.

Figure 14:
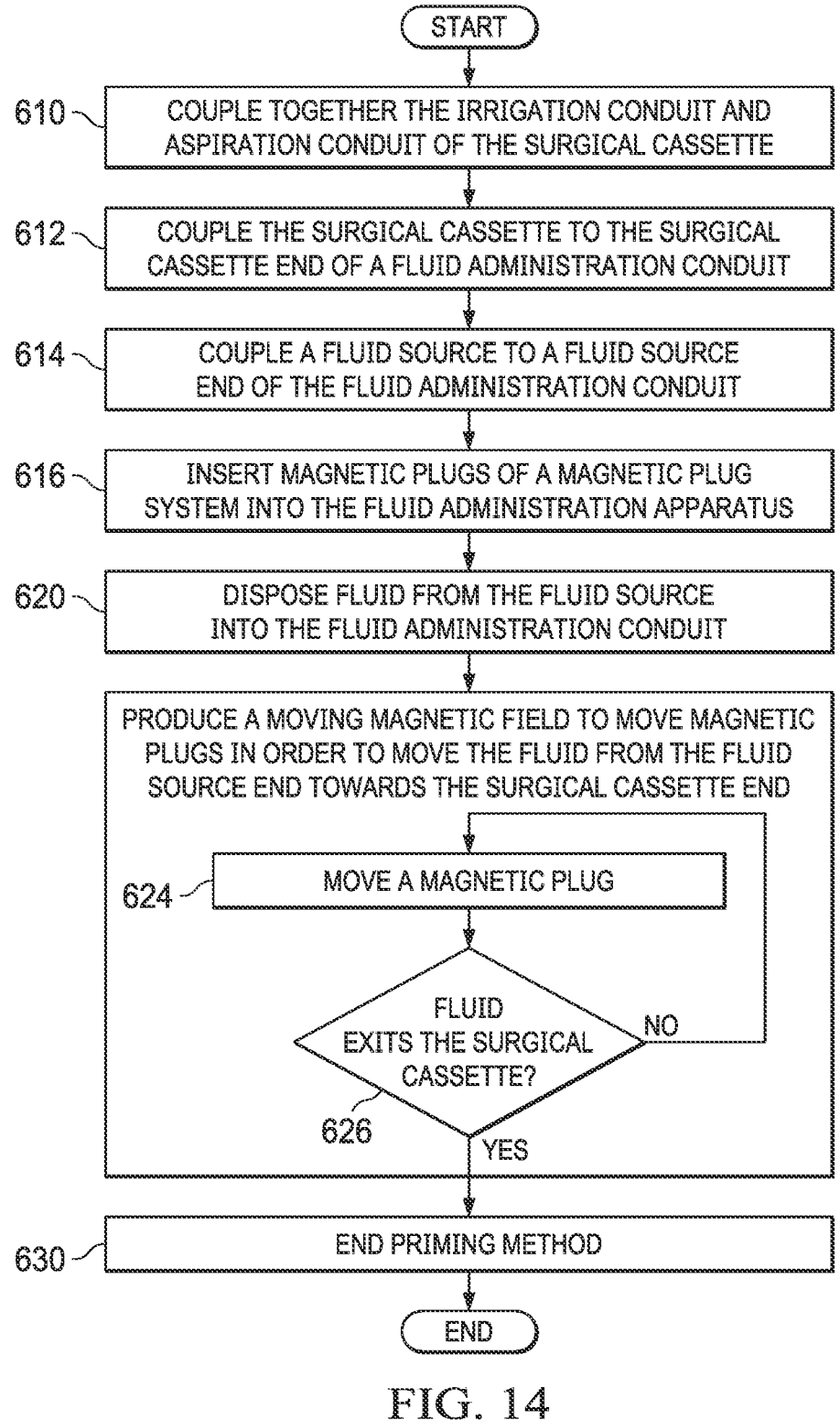
FIG. 14 illustrates an example of a method that may be used by the priming system of FIG. 12 to prime a surgical cassette.

FIG. 14 illustrates an example of a method that may be used by priming system 510 of FIG. 12 to prime surgical cassette 512. The method starts at step 610, where irrigation conduit 320 and aspiration conduit 322 of surgical cassette 512 are coupled together. The coupling allows fluid exiting surgical cassette 512 via irrigation conduit 320 to reenter surgical cassette 512 via aspiration conduit 322. Surgical cassette 512 is coupled to surgical cassette end 526 of fluid administration conduit 522 of fluid administration apparatus 516 of priming system 10 at step 612. Fluid source 544 is coupled to fluid source end 524 of fluid administration conduit 522 at step 614.

Magnetic plugs 514 of a magnetic plug system are inserted into fluid administration apparatus 516 at step 616. In certain embodiments, a plurality of magnetic plugs 514 (e.g., plugs A and B) are inserted into plug entrance 530, and at least one magnetic plug 514 (e.g., plug C) into plug exit 532. Plug A in entrance 530 may be moved towards plug insertion port 536 and secured into place, and plug C in exit 532 may be moved towards plug extraction port 542 and secured into place. A magnetic plug 514 may be moved and secured into place in any suitable manner. For example, a plug 514 may be moved by hand, or a magnet 520 may be moved to create a moving magnetic field that moves the plug 514. As another example, a clamp may be applied to prevent movement of a plug 514, or a magnet 520 may be secured to secure the plug 514 in place.

Fluid from fluid source 544 is disposed into fluid administration conduit 522 at step 620. In certain embodiments, fluid 544 may be a bag that can be squeezed to push the fluid into conduit 522. In certain embodiments, plugs A and C block the fluid from flowing into plug entrance 530 and plug exit 532. The fluid enters conduit 522 and surgical cassette 512.

At steps 624 and 626, a moving magnetic field is produced to move magnetic plugs 514, which move the fluid from fluid source end 524 towards surgical cassette end 526. The fluid is moved until fluid exits surgical cassette 512, indicating that surgical cassette 512 is primed for surgery.

A magnetic plug 514 is moved from plug entrance 530 towards plug exit 532 at step 624. In certain embodiments, plug A in plug entrance 530 may be moved (e.g., pushed by squeeze applicator 532) into conduit 522 through plug insertion port 536. Entrance magnet 520*b* may be deactivated (e.g., removed from apparatus 516) to allow plug A to be moved. Plug B may be secured into place in entrance 530 to prevent it from moving into conduit 522 and to allow it to block fluid from flowing into plug entrance 530. Entrance magnet 520*b* may be activated (e.g., attached to apparatus 516) to secure plug B.

In the embodiments, to move plug A from plug entrance 530 towards plug exit 532, conduit magnet 520*a* may be disposed around conduit 522. Conduit magnet 520*a* may then attract plug A located at plug insertion port 536 and pull it away from entrance magnet 520*b*. Conduit magnet 520*a* is moved along conduit 522 towards plug exit 532, while more fluid from fluid source 544 is added into fluid administration conduit 522. The fluid may be added by, e.g., squeezing fluid source 544. When conduit magnet 520*a* reaches plug exit 532, plug A is attracted by and couples to plug C located in plug exit 532. Exit magnet 520*c* secures plugs A and C at plug exit 532, which prevent fluid from entering plug exit 532.

Fluid may exit surgical cassette 512 at step 626, which indicates surgical cassette 512 is primed. If fluid does not exit, the method returns to 624 to move the next magnetic plug 514. Plug B may be moved in a manner similar to that of plug A. If fluid exits surgical cassette 512 at step 626, the method proceeds to step 630, where the priming method ends.

In certain embodiments, primed surgical cassette 512 may be prepared prior to surgery. To prevent fluid from exiting conduit 522, entrance and exit magnets 540*b* and 540*c* may be secured in place to secure magnetic plugs 514 in place in plug entrance 530 and plug exit 532 in order block the fluid.

A component (such as a computer or controller of the embodiments herein) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speaker.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. A fluid management system for an ophthalmic surgical system, the fluid management system comprising:
   an irrigation system in fluid communication with a handpiece and configured to carry fluid toward the handpiece, the irrigation system comprising:
   an irrigation pump of a plurality of pumps, the irrigation pump configured to move the fluid toward the handpiece; and
   an aspiration system in fluid communication with the handpiece and configured to carry fluid away from the handpiece, the aspiration system comprising:
   an aspiration pump of the plurality of pumps, the aspiration pump configured to move the fluid away from the handpiece,
   the plurality of pumps comprising at least one magnetic pump configured to move the fluid, the magnetic pump comprising:
   a plug system comprising two or more plugs disposed within a housing, each plug comprising a magnetic material; and
   a magnetic field system configured to generate a magnetic field to move the two or more plugs in order to move the fluid between the two or more plugs in a pumping direction.

2. The fluid management system of claim 1, the magnetic field system comprising a coil system configured to generate the magnetic field, the coil system comprising one or more electromagnetic coils disposed about the housing.

3. The fluid management system of claim 2, the coil system comprising a plurality of coils comprising:

a first coil configured to generate the magnetic field to move the two or more plugs; and a second coil successive to the first coil and configured to generate the magnetic field to continue to move the two or more plugs in the pumping direction.

4. The fluid management system of claim 1, the magnetic field system comprising a magnet system configured to generate the magnetic field, the magnet system comprising one or more magnets disposed about the housing.

5. The fluid management system of claim 4, the magnet system comprising a magnet configured to move to yield a moving magnetic field that moves the two or more plugs in the pumping direction.

6. The fluid management system of claim 1, the housing comprising tubing or a chamber with a rectangular box shape.

7. The fluid management system of claim 1, the magnetic field system configured to generate the magnetic field in a direction substantially parallel to the pumping direction.

8. The fluid management system of claim 1, the magnetic field system configured to generate the magnetic field in a direction substantially orthogonal to the pumping direction.

9. The fluid management system of claim 1, further comprising a controller configured to coordinate the at least one magnetic pump.

10. A handpiece for an ophthalmic surgical system, the handpiece comprising:

an irrigation channel in fluid communication with an irrigation system and configured to carry fluid from the irrigation system;

an aspiration channel in fluid communication with an aspiration system and configured to carry fluid toward the aspiration system; and a magnetic pump configured to move the fluid, the magnetic pump comprising:

a plug system comprising two or more plugs disposed within a housing, each plug comprising a magnetic material; and a magnetic field system configured to generate a magnetic field to move the two or more plugs in order to move the fluid between the two or more plugs in a pumping direction.

11. The handpiece of claim 10, the pumping direction moving the fluid from the irrigation system.

12. The handpiece of claim 10, the pumping direction moving the fluid toward the aspiration system.

13. A fluid management system for an ophthalmic surgical system, the fluid management system comprising:

an irrigation system in fluid communication with a handpiece and configured to carry fluid in a housing toward the handpiece, the fluid comprising a plurality of ferromagnetic nanoparticles to yield a ferrofluid, the irrigation system comprising:

an irrigation pump of a plurality of pumps, the irrigation pump configured to move the fluid toward the handpiece; and an aspiration system in fluid communication with the handpiece and configured to carry fluid in the housing away from the handpiece, the aspiration system comprising:

an aspiration pump of the plurality of pumps, the aspiration pump configured to move the fluid away from the handpiece, the plurality of pumps comprising at least one magnetic pump configured to move the fluid, the magnetic pump comprising:

a magnetic field system configured to generate a magnetic field to move the fluid comprising the ferromagnetic nanoparticles in a pumping direction.

14. The fluid management system of claim 13, the magnetic field system comprising a coil system configured to generate the magnetic field, the coil system comprising one or more electromagnetic coils disposed about the housing.

15. The fluid management system of claim 13, the magnetic field system comprising a magnet system configured to generate the magnetic field, the magnet system comprising one or more magnets disposed about the housing.

* * * * *